US010195599B2

(12) United States Patent
Biradar et al.

(10) Patent No.: US 10,195,599 B2
(45) Date of Patent: Feb. 5, 2019

(54) SYNTHESIS OF FUNCTIONALIZED CARBON MICROSPHERES AND THEIR CATALYST ACTIVITY IN C—O AND C—N BOND FORMATION REACTIONS

(71) Applicant: COUNCIL OF SCIENTIFIC AND INDUSTRIAL RESEARCH, New Dehli (IN)

(72) Inventors: Ankush Venkatrao Biradar, Pune (IN); Shubhangi Bhalchandra Umbarkar, Pune (IN); Mohan Keraba Dongare, Pune (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 15/911,018

(22) Filed: Mar. 2, 2018

(65) Prior Publication Data

US 2018/0229225 A1 Aug. 16, 2018

Related U.S. Application Data

(62) Division of application No. 14/901,456, filed as application No. PCT/IN2014/000423 on Jun. 25, 2014, now Pat. No. 10,029,240.

(30) Foreign Application Priority Data

Jun. 25, 2013 (IN) .......................... 1877/DEL/2013

(51) Int. Cl.
*C07D 301/12* (2006.01)
*C07C 205/09* (2006.01)
*C07C 205/00* (2006.01)
*B01J 31/02* (2006.01)
*B01J 21/18* (2006.01)
*B01J 35/00* (2006.01)
(Continued)

(52) U.S. Cl.
CPC .......... *B01J 31/0237* (2013.01); *B01J 21/18* (2013.01); *B01J 31/0205* (2013.01); *B01J 31/0225* (2013.01); *B01J 31/08* (2013.01); *B01J 31/10* (2013.01); *B01J 35/002* (2013.01); *B01J 35/08* (2013.01); *B01J 37/0209* (2013.01); *B01J 37/084* (2013.01); *C01B 32/05* (2017.08); *C07C 201/14* (2013.01); *C07D 301/12* (2013.01); *B01J 2231/342* (2013.01); *B01J 2231/4205* (2013.01); *B01J 2231/72* (2013.01)

(58) Field of Classification Search
CPC .... B01J 31/0237; B01J 31/0205; B01J 31/08; B01J 31/10; B01J 31/0225; B01J 35/002; B01J 35/08; B01J 37/0209; B01J 37/084; B01J 21/18; C07C 201/14; C07C 205/00; C07C 205/09; C07D 301/12; C01B 32/05
USPC ....................... 502/8; 549/531; 568/705, 927
See application file for complete search history.

(56) References Cited

PUBLICATIONS

Hu, Bo, et al., "Engineering Carbon Materials from the Hydrothermal Carbonization Process of Biomass," *Advanced Materials*, Wiley— VCH Verlag GmbH & Co., KGaA, De, vol. 22, No. 7, Feb. 16, 2010, pp. 813-828.

(Continued)

*Primary Examiner* — Taylor V Oh
(74) *Attorney, Agent, or Firm* — Lewis Roco Rothgerber Christie LLP (57) ABSTRACT

Disclosed herein is a simple process for functionalization/ grafting of carbon microspheres obtained from bagasse with various active functional groups onto it and use of the same as catalyst for various organic reactions, having very high selectivity and conversion rate.

4 Claims, 7 Drawing Sheets

(51) Int. Cl.
*B01J 35/08* (2006.01)
*B01J 37/02* (2006.01)
*B01J 31/08* (2006.01)
*B01J 31/10* (2006.01)
*B01J 37/08* (2006.01)
*C07C 201/14* (2006.01)
*C01B 32/05* (2017.01)

(56) References Cited

PUBLICATIONS

Liu, Jie, et al., "Hydrothermal Synthesis of Carbon Microspheres from Glucose: Tuning Sphere Size by Adding Oxalic Acid," *Chemistry Letters*, vol. 38, No. 10, Aug. 29, 2009, pp. 948-949.
Liu, Weifeng, et al., "Reactive carbon microspheres prepared by surface-grafting 4-(chloromethyl)phenyltrimethoxysilane for preparing molecularly imprinted polymer," *Applied Surface Science*, Elsevier, Amsterdam, NL, vol. 277, Apr. 11, 2013, pp. 146-154.
Yaman, "Pyrolysis of Biomass to produce fuels and chemical feedstocks," Energy Conversion and Management, 2004, 45, p. 651-671.
Yang, Yongzhen, et al., "Grafting molecularly imprinted poly(2-acrylamido-2-methylpropanesulfonic acid) onto the surface of carbon microspheres," *Applied Surface Science*, Elsevier, Amsterdam, NL, vol. 258, No. 17, Mar. 12, 2012, pp. 6441-6450.
Wikipedia, "Bagasse," Aug. 4, 2012, p. 1-5.
PCT International Search Report and Written Opinion dated Jan. 15, 2015 for PCT/IN2014/000423, 17 pgs.

Figure: 9B

SYNTHESIS OF FUNCTIONALIZED CARBON MICROSPHERES AND THEIR CATALYST ACTIVITY IN C—O AND C—N BOND FORMATION REACTIONS

CROSS-REFERENCED TO RELATED APPLICATION(S)

This application is a divisional application of U.S. patent application Ser. No. 14/901,456, filed Dec. 28, 2015, which is a National Phase Patent Application and claims priority to and the benefit of International Application No. PCT/IN2014/000423, filed Jun. 25, 2014, which claims priority to and the benefit of Indian Application No. 1877/DEL/2013, filed Jun. 25, 2013, the entire contents of all of which is hereby expressly incorporated herein by reference.

TECHNICAL FIELD OF THE INVENTION

The present invention relates to a simple process for functionalization/grafting of carbon microspheres obtained from bagasse with various active functional groups onto it and their catalyst activity in C—O and C—N bond formation reactions with high selectivity and conversion rate.

BACKGROUND AND PRIOR ART

Carbon is a versatile element because of its unique ability to form complexes in which the carbon atom has sp, $sp^2$ and $sp^3$ electronic configurations resulting in a wide range of structures and morphologies with widespread applications (Kang Z. C. and Wang Z. L, *Mol. Catal. A: Chemical* 118, 215-222). The search for new synthetic strategies for generating nanostructured carbon or carbon-hybrid materials is current in material chemistry, motivated by the natural abundance of carbon and therefore the cost effectiveness of carbon precursors and the promising applications of the resulting materials. Due to the intrinsic properties of the carbon materials, such as their high strength, high thermal resistance and light weight, carbon microspheres (CMS) can be used as high-strength composites, catalyst supports, lubricants and as wear-resistant materials (Jin Y. Z. et al 2005, *Carbon* 43, 1944-53).

High surface area mesoporous carbon materials (activated carbon) are important materials which are largely used in the industry for various applications e.g. pollution control treatment, water treatment and as a support in heterogeneous catalysts.

Different processes have been used to synthesize sphere like forms of carbon. N. J. Coville et al. have achieved the production of pure carbon spheres in the absence of a catalyst through the direct pyrolysis of hydrocarbon sources, acetylene and ethylene. Carbon microsphere-supported cobalt catalysts were synthesized and have shown good activity in the ethylene hydrogenation reactions (*South African Journ. of Sci.* 105, July/August 2009, 304-8).

Conventionally these carbon materials are synthesized by carbonization of various carbon sources such as coal, coconut hulls, acid sludges, petroleum coke and wood. These synthesized carbon materials have excellent physical properties such as high surface area and is inert in nature.

However, these high surface area materials when used in catalysis or as supports have very little influence on the reaction and the supporting active metal loaded on the carbon material leaches out resulting in deactivation of the catalyst and rendering it useless. This can be avoided either by protecting with hydroxyl groups or grafting various functional groups onto the surface of carbon which allows the introduction of additional functionality to tailor its surface and interfacial properties for the desired application. Due to the inert nature of carbon harsh reaction conditions are required for its functionalization. Frequently used carbon surface functionalization methodologies are aryl radicals coupling, amines, coupling of alkynes and azides at high temperatures. Recently carbon was functionalized by gas phase azide condensation method (*J. Am. Chem. Soc.*, 2013, 135 (3), pp 1110-1116) which shows the importance of functionalization of carbon microspheres. As these methods need high temperature and many expensive chemicals there is a need for alternative route for functionalization of carbons.

Maria-Magdalena Titirici et al, (*Chem. Mater.* 2009, 21, 484-490) provides a one-step aqueous route production of carbon microspheres loaded with carboxylic groups and hydroxyl groups using hydrothermal carbonization (HTC) of glucose in the presence of acrylic acid. The resulting carboxy groups on the surface of the carbon microspheres can be used for further functionalization aiming at different applications.

Furthermore, Shu-Hong Yu et al (*Dalton Trans.*, 2008, 5414-5423) and Ying liang Liu, (*J. Phys. Chem. C*, 2009, 113 (19), 8455-59) disclose hydrothermal carbonization (HTC) process of biomass to produce functional carbonaceous materials.

Reference made to Chemistry Letters Vol. 38, No. 10 (2009) where glucose which is a 6-carbon sugar and Oxalic acid a strong organic acid has been used for synthesis of carbon microspheres. During synthesis of CMS under HTC carbonization it has to dehydrate and polymerization to form carbon spheres. Being used Oxalic acid it degrade and form water and end up with less surface hydroxyl groups. Being less functional onto surface of CMS the functionalization of other groups was not occurred. However in the present invention: Bagasse is used which mainly contains cellulose, pentosan, and lignin, which are polymers of large groups of carbons and upon HTC carbonation with Oxalic acid it does not dehydrate but only condensation and self assemble happen which leads to large number of hydrophilic functionalities —OH, —C=O, and COOH groups over carbon spheres and due to this very high available co-functional groups the grafting of other functional was possible.

However, there is still a need in the art to provide a process for grafting catalytically active functional groups on to the functionalized carbon microspheres and to derive a stable catalyst for various organic reactions.

OBJECTIVE OF THE INVENTION

The main object of the invention is to provide a simple process for grafting/functionalizing active functional groups on to functionalized carbon microspheres obtained from bagasse and their catalyst activity in C—O and C—N bond formation reactions with high selectivity and conversion rate.

SUMMARY OF THE INVENTION

Accordingly, the present invention provides a process for preparation of functionalized carbon microspheres by grafting catalytically active functional groups on to carbon microspheres obtained from bagasse to generate acidic or basic surface wherein said process comprising the steps of;

a) heating bagasse, water and oxalic acid at temperature ranging between 150 to 180° C. for a period ranging between 6 to 12 h to obtain carbon microspheres;
b) refluxing of carbon microspheres as obtained in step (a) and an organic solvent selected from the group consisting of n-pentane, n-hexane, toluene or lower alcohols in the presence of functional group grafting agent at temp ranging between 80-120° C. for a period in the range of 8-12 h to obtain functionalized carbon microspheres.

In an embodiment of the invention functional group grafting agent in step (b) is selected from the group consisting of 3-aminopropyltrimethoxysilane (APTMS) (3-(2aminoethylamino) propyl)-trimethoxysilane, (3-(mecaptopropyl)-trimethoxy sila, 3-cyanopropyltriethoxysilane.

In one embodiment of the invention the active functional groups are selected from the group consisting of silylated acid, amine, $SO_3H$ groups to obtain acidic, or basic functional characteristics.

In another embodiment of the invention the diameter or the particle size of functionalized CMS is 1 to 5 µm.

In another embodiment of the invention the said functionalized carbon microspheres catalyze C—O and C—N bond formation reactions in high selectivity and conversion rate.

Still in another embodiment of the invention C—O formation reactions is epoxidation process which comprises mixing olefin, an oxidant $H_2O_2$, an organic solvent acetonitrile and amine functionalized carbon microspheres to obtain a reaction mixture followed by immersing the reaction mixture in thermostat oil bath at temperature ranging between 60-80° C. for a period ranging between 24-48 h to obtain the epoxide with yield in the range of 45-90% and conversion in the range of 45-95%.

Still in another embodiment of the invention olefin is selected from the group consisting of cyclic olefines selected from the group consisting of Cyclohexene, Cyclococetene, 1,3 cyclohexene, Pentene, 1,5 cyclooctadiene.

Still in another embodiment of the invention epoxide is produced from the group consisting of cyclic epoxides consists of Cyclohexeneepoxide, Cycloocene epoxide, Penteneoxide-oxabicyclo[4.1.0]hept-2-ene 1, Z)-9-oxabicyclo [6.1.0]non-4-ene Still in another embodiment of the invention C—N bond formation reactions is nitroaldol reactions which comprises mixing substituted benzaldehyde, nitromethane and amine functionalized carbon microspheres to obtain a reaction mixture followed by immersing the reaction mixture in thermostat oil bath at temperature in the range of 70-100° C. for a period in the range of 0.5-35 h to obtain nitroalcohol and nitrostyrene with yield in the range of 30 to 95% and conversion in the range of 10 to 98%.

Still in another embodiment of the invention substituted benzaldehyde is selected from the group consisting of p-hydroxyl benzaldehyde, Benzaldehyde or p-hydroxybenzaldehyde.

BRIEF DESCRIPTION OF THE DRAWINGS

FIG. 2 depicts the $^{13}C$ NMR of carbon microspheres prepared at different conditions.
FIG. 3 depicts the $^{13}C$ NMR of amine functionalized carbon microspheres.
FIG. 4 depicts the $^{29}Si$ NMR of amine functionalized CMS.
FIG. 5 depicts the P-XRD of amine functionalized CMS
FIG. 6 depicts the thermo-gravimetric analysis (TGA) of prepared amines-CMS
FIGS. 9A and 9B depict the FTIR of CMS and OX-CMS (oxidized-CMS)

DETAILED DESCRIPTION OF THE INVENTION

The present invention relates to a process for grafting catalytically active functional groups on to the functionalized carbon microsphere (CMS) obtained from bagasse to generate acidic or basic surface, wherein said grafted carbon microsphere is stable and can be used as a catalyst in various organic reactions comprising;
a) heating a mixture of bio derived material and distilled water, optionally in the presence of an acid to a temperature in the range of 180-210° C. for 4 to 12 h, to obtain functionalized carbon microspheres as black solid, and
b) dispersing the black solid obtained in step (a) in dry toluene and adding functional groups for post grafting followed by refluxing for 8 h to yield corresponding grafted/functionalized carbon microsphere.

The bio derived material used in step (a) of the process is selected bagasse which mainly contain of cellulose, pentosan, and lignin as a carbon source.

The organic solvent used in step (b) of the process is selected from aliphatic or aromatic hydrocarbons such as n-pentane, n-hexane, toluene or lower alcohols.

The functionalized carbon microspheres obtained in step (a) are post grafted with functional groups selected from, but not limited to the group consisting of silylated acid, amine, $SO_3H$ groups to obtain acidic, basic or bi functional characteristics.

The grafted/functionalized CMS prepared by the process of the instant invention can be used as metal free catalyst for various organic reactions that generate C—N and C—O bond formation, which generates no hazardous byproduct, and has very high conversion rate of substrate. Further, the grafted/functionalized CMS can also be used as support for dispersing various active components on them.

The diameter or the particle size of grafted/functionalized CMS prepared by the process of the instant invention having active functional groups is in the range of 1-5 µM.

The present invention provides a grafted/functionalized carbon microsphere comprising active functional groups selected from, but not limited to the group consisting of silylated acid, amine, $SO_3H$ groups thereby having acidic or basic surface, wherein the said grafted carbon microsphere is stable and useful as catalyst in various organic reactions The grafted/functionalized CMS prepared by the process of the instant invention due to their further functionalized nature imparts structural stability to the said carbon microsphere when used as catalysts or active component and does not leach out during organic reactions, leading to an efficient recyclable catalyst.

The present invention discloses a simple one step process for the synthesis of functionalized carbon microspheres (CMS) comprising mixing bio derived material with distilled water to obtain a mixture and heating to 180-210° C. for 4 to 12 h, in the presence of an acid, to afford the product as black solid.

The surface of the CMS so obtained contain hydroxyl, carboxyl, esters, ethers, carbonyl groups, that provide ease in functionalization to create hydrophilic and hydrophobic surface using a short-chain diol, acid or a long-chain alkylamine.

The biomass is selected from celluloses, sugars such as glucose, fructose, sucrose bagasse and such like.

Figure 1:
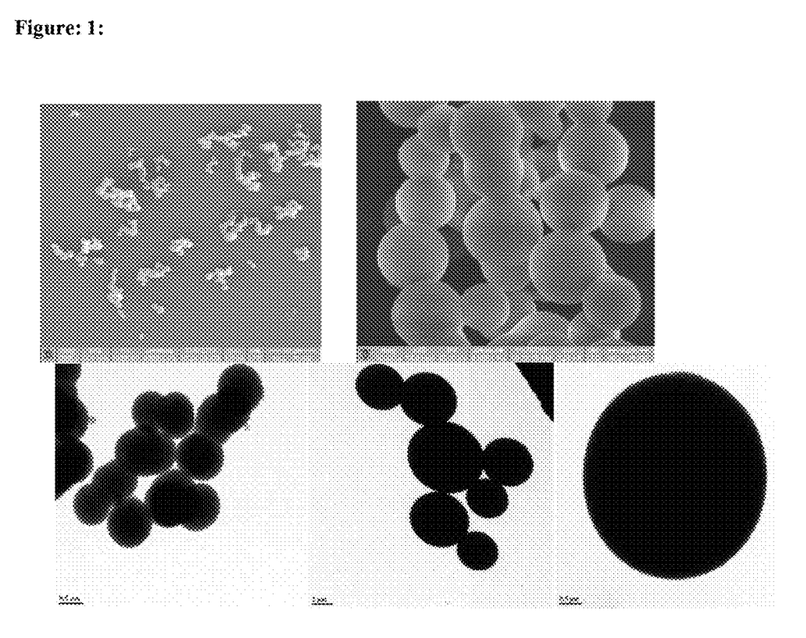
FIG. 1 depicts the TEM of carbon microspheres.
Figure 7:
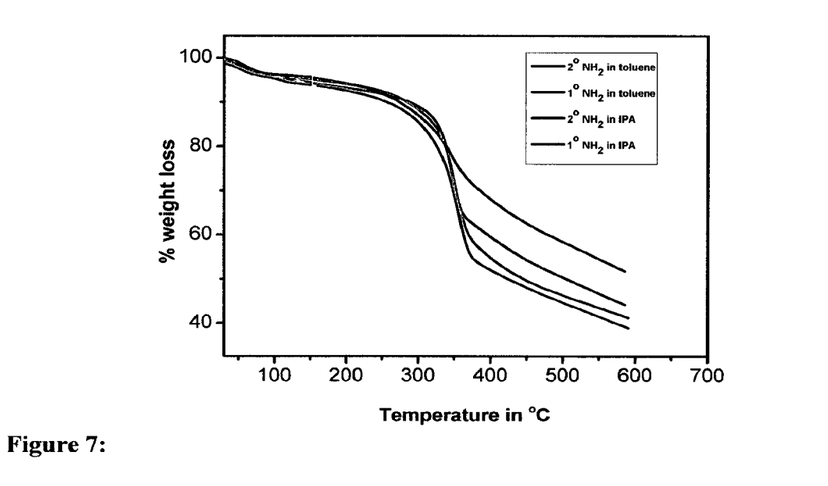
FIG. 7 depicts FTIR (Fourier transform infrared spectroscopy) of CMS and amine functionalized ($NH_2$) CMS.

The acid is selected from the group consisting of oxalic acid, succinic acid, glutaric acid, adipic acid and such like. The carbon microsphere obtained are uniform microspheres of porous carbon and have diameter in the range of 1-10 µm; preferably 4-5 µm. Further, the synthesized CMS are characterized by SEM, TEM, FTIR and NMR. Transmission electron microscopy (TEM) measurements were performed on a Tecnai G2-20 FEI instrument operating at an accelerating voltage at 200 kV, refer FIG. 1. Samples were withdrawn periodically and analysed on Agilent 6890 Gas chromatograph equipped with a HP-5 dimethyl polysioxane column (60 m length, 0.25 mm diameter and 0.25 µm film thicknesses with flame ionization detector. Products were confirmed by injecting the authentic on GC and GCMS.

The present invention provides use of functionalized/grafted carbon microspheres (CMS) as catalyst for organic reactions which generates that generate C—N and C—O bond formation with high conversion rate of the substrate. The present invention provides an epoxidation process of 90% conversion and 96% selectivity catalyzed by the instant carboxyl functionalized carbon microspheres comprising:
  a. mixing Olefin, $H_2O_2$, Acetonitrile and carboxyl functionalized carbon microspheres as prepared above to obtain a reaction mixture and
  b. immersing the reaction mixture obtained in step (a) in thermostat oil bath at 80° C. for 48 h to obtain the desired epoxide.

The present invention provides the nitroaldol reaction/Henry reaction catalyzed by the instant amine functionalized carbon microspheres comprising:
  a) mixing hydroaldehyde, nitromethane and amine functionalized carbon microspheres as prepared above to obtain a reaction mixture; and
  b) immersing the reaction mixture obtained in step (a) in thermostat oil bath at 90° C. for 2 h to obtain the desired product.

The process is shown in Scheme 1 below:

A: p-hydroxy benzaldehyde, B: nitromethane, C: 2-nitro-1-phenyl ethanol, D: β-nitrostyrene, and E: 1-3 dinitropropan-2-yl) benzene The % conversion obtained is 100% and % product selectivity is 90% of β-nitrostyrene as the major product obtained in Henry reaction. Recyclability studies performed using the instant catalyst indicated 100% conversion and 100% selectivity.
(Table 1)

Thus the present invention provides an efficient tethering of the active organic acid and/or base functional groups onto a robust carbon support which will be metal free catalyst for various organic reactions which generates minimum hazardous byproduct, having very high conversion of substrate and yielding as the nitroaldol and epoxide as products.

EXAMPLES

The following examples are given by way of illustration of working of the invention in actual practice and should not be constructed to limit the scope of the present invention in any way

Example 1

Synthesis of Carbon Microspheres (CMS) from Cellulose:
  100 mL stainless steel reactor was charged with 4 gm of cellulose, 50 mL distilled water and 0.25 gm of oxalic acid and reactor was closed and kept static at 180° C. for 8 h. Then reactor was cooled to room temperature (25° C.). The black solid was collected by and filtered under vacuum using whatman filter paper no 41 and washed with water (4×100 mL) followed by ethanol (2×50 mL) and final product was dried at room temperature (25° C.). Product weight—1.02 g

Example 2

Synthesis of Carbon Microspheres (CMS) from Bagasse:
  100 mL stainless steel reactor was charged with 4 gm of bagasse (sample of bagasse was taken from Vikas SSK limited, Vaishali Nagar, Nivali Taluka & Dist—Latur, Maharashtra), 50 mL distilled water and 1 gm of oxalic acid and reactor was closed and kept static at 180° C. for 12 h. Then reactor was cooled to room temperature (25° C.). The black solid was collected by and filtered under vacuum using whatmann filter paper no 41 and washed with water (4×100 mL) followed by ethanol (2×50 mL) and final product was dried at room temperature (25° C.). Product weight—1.09 g

Example 3

Figure 8:
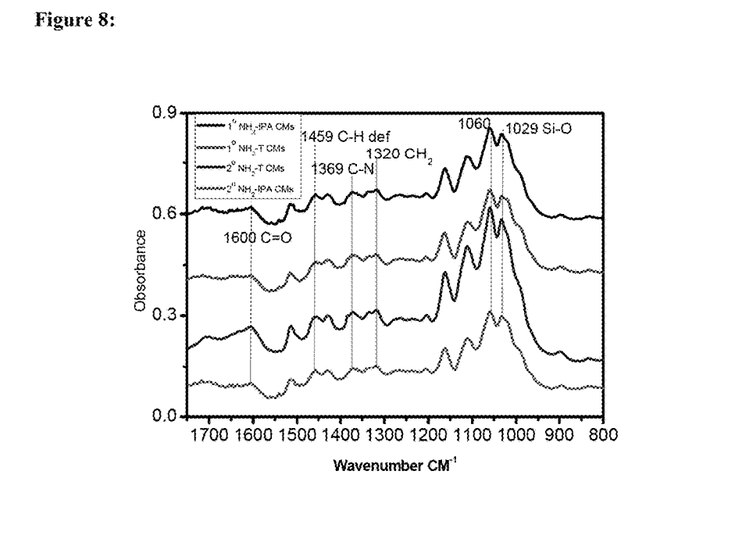
FIG. 8 depicts the CHN (elemental) analysis of CMS and amine functionalized ($NH_2$) CMS.

Synthesis of Amine Functionalized Carbon Microspheres (CMS) in Toluene:
  The functionalization of CMS was carried out in a two necked round bottom flask fitted with water condenser charged with 1 g of carbon microspheres as obtained in example 2 and 200 mL dry toluene and 1 gm of 3-aminopropyltrimethoxysilane (APTMS). The reaction mixture was refluxed for 8 h 110° C. followed by cooling the reaction mixture to room temperature (25° C.) and filtering it by vacuum and washed with toluene (3×25 mL) and dichloromethane (2×25 mL) and finally with ethanol (2×25 mL). Final reaction mixture was dried at room temperature (25° C.). Product weight—0.512 g CHN analysis given in FIG. 8

Example 4

Synthesis of Amine Functionalized Carbon Microspheres (CMS) in IPA:
  The functionalization of CMS was carried out in a two necked round bottom flask fitted with water condenser charged with 0.5 g of carbon microspheres as obtained in example 2 and 200 mL dry isopropyl alcohol and 0.5 gm of aminopropyltrimethoxysilane (APTMS). The reaction mixture was refluxed for 8 h at 80° C. then the reaction mixture was cooled to room temperature (25° C.) and filtered by vacuum and washed with toluene (3×25 mL) and dichloromethane (2×25 mL) and finally with ethanol (2×25 mL). Final reaction mixture was dried at room temperature (25° C.). Product weight—0.504 g Example 5

Synthesis of 2° Amine Functionalized Carbon Microspheres (CMS) in Toluene:

The functionalization of CMS was carried out in a two necked round bottom flask fitted with water condenser charged with 1 g of carbon microspheres as obtained in example 2 and 200 mL dry toluene and 1 gm of (3-(2aminoethylamino) propyl)-trimethoxysilane. The reaction mixture was refluxed for 8 h 110° C. followed by cooling the reaction mixture to room temperature (25° C.) and filtering it by vacuum and washed with toluene (3×25 mL) and dichloromethane (2×25 mL) and finally with ethanol (2×25 mL). Final reaction mixture was dried at room temperature (25° C.). Product weight—0.512 g CHN analysis given in FIG. 8

Example 6

Synthesis of 2° Amine Functionalized Carbon Microspheres (CMS) in IPA:

The functionalization of CMS was carried out in a two necked round bottom flask fitted with water condenser charged with 1 g of carbon microspheres as obtained in example 2 and 200 mL dry isopropyl alcohol and 1 gm of (3-(2aminoethylamino) propyl)-trimethoxysilane. The reaction mixture was refluxed for 8 h 80° C. then the reaction mixture was cooled to room temperature (25° C.) and filtered by vacuum and washed with toluene (3×25 mL) and dichloromethane (2×25 mL) and finally with ethanol (2×25 mL). Final reaction mixture was dried at room temperature (25° C.). Product weight—0.504 g Example 7

Synthesis of $SO_3H$ Functionalized Carbon Microspheres (CMS) in Toluene:

The functionalization of CMS was carried out in a two necked round bottom flask fitted with water condenser charged with 0.5 g of carbon microspheres as obtained in example 2 and 200 mL dry isopropyl alcohol and 0.5 gm of (3-(mecaptopropyl)-trimethoxy silane. The reaction mixture was refluxed for 8 h at 110° C. then the reaction mixture was cooled to room temperature (25° C.) and filtered by vacuum and washed with toluene (3×25 mL) and dichloromethane (2×25 mL) and finally with ethanol (2×25 mL). Final reaction mixture was dried at room temperature (25° C.) named as SH-CMS Product weight—0.510 g Then 0.5 gm SH-CMs was dispersed in 25 mL of toluene and added 5 mL of 30% $H_2O_2$ and stirred at room temperature for 24 hr. then filtered and washed with water and ethanol and dried at room temperature. Yield: 0.425 gm.

Example 8

Synthesis of COOH Functionalized Carbon Microspheres (CMS) in Toluene:

The functionalization of CMS was carried out in a two necked round bottom flask fitted with water condenser charged with 1 g of carbon microspheres as obtained in example 2 and 250 mL dry toluene and 1 mL gm of 3-cyanopropyltriethoxysilane. The reaction mixture was refluxed for 24 h at 110°. then the reaction mixture was cooled to room temperature (25° C.) and filtered by vacuum and washed with toluene (3×25 mL) and dichloromethane (2×25 mL) and finally with ethanol (2×25 mL). Final reaction mixture was dried at room temperature (25° C.) named as CNCMs.

Product weight—1.110 g and product were characterized with FTIR.

Then 0.5 gm CN-CMs was dispersed in 25 mL of toluene and added 5 mL of 70% $H_2SO_4$ and stirred at room temperature for 24 hr. then filtered and washed with water and ethanol and dried at room temperature. Yield: 0.425 gm.

Example 9

Synthesis of COOH Functionalized Carbon Microspheres (CMS)

The functionalization of CMS was carried out in a two necked round bottom flask fitted with water condenser charged with 1 g of carbon microspheres as obtained in example 2 and 4.5 ml of conc.$HNO_3$. The reaction mixture was heated at 90° C. for 6 h. then the reaction mixture was cooled to room temperature (25° C.) and filtered by vacuum and washed with acetone (3×25 mL) and water (2×25 mL) and finally with ethanol (2×25 mL). Final reaction mixture was dried at room temperature (25° C.) named as COOH—CMs Product weight—0.350 g and product were characterized with FTIR See FIG. 9.

Example 10

Nitroaldol Reaction

The liquid phase Henry reaction was carried out in a two necked round bottom flask fitted with water condenser charged with substituted benzaldehyde (0.01 mol) and Nitromethane—8 ml and 10 mg of amine functionalized carbon microspheres as prepared in example 4. The reaction was initiated by immersing in a thermostat oil bath at 90° C. and stirring at 600 pm. The reaction was carried out for till completion. The samples were withdrawn periodically and analysed on Agilent 6890 Gas chromatograph. Results are summarised in table 1.

TABLE 1

% Conversion and % selectivity of catalyst

| Sr. No. | Sustrate | Catalyst | Time (H) | % Con | Selectivity (%) alcohol | Styrene |
|---|---|---|---|---|---|---|
| 1 | P-nitrobenzaldehyde | CMS before functionalization | 30 | 0 | 0 | 0 |

TABLE 1-continued

| | | | | | Selectivity (%) | |
|---|---|---|---|---|---|---|
| Sr. No. | Sustrate | Catalyst | Time (H) | % Con | alcohol | Styrene |
| 2 | P-nitrobenzaldehyde | Functionalized CMS obtained from glucose | 30 | 0 | 0 | 0 |
| 3 | P-nitrobenzaldehyde | 1° NH$_2$ in T | 8.30 | 28 | — | 100 |
| | | | 28 | 78 | — | 100 |
| 4 | P-nitrobenzaldehyde | 1° NH$_2$ in IPA | 10 | 20 | — | 100 |
| | | | 35 | 100 | 29 | 71 |
| 5 | P-nitrobenzaldehyde | 2° NH$_2$ in T | 9 | 78 | — | 100 |
| | | | 22 | 79 | — | 100 |
| 6 | P-nitrobenzaldehyde | 2° NH$_2$ in IPA | 35 | 69 | — | 100 |
| 7 | Benzaldehyde | CMS | 0 | 0 | 0 | 0 |
| 8 | Benzaldehyde | 1° NH$_2$ in T | 6 | 40 | 59 | 41 |
| 9 | Benzaldehyde | 2° NH$_2$ in T | 4 | 98 | 43 | 57 |
| 10 | p-hydroxybenzaldehyde | CMS | 0 | 0 | 0 | 0 |
| 11 | p-hydroxybenzaldehyde | 1° NH$_2$ in T | 30 min | 100 | 100 | 0 |
| 12 | p-hydroxybenzaldehyde | 2° NH$_2$ in T | 30 min | 100 | 6 | 94 |

Reaction Conditions: p-nitro benzaldehyde/Benzaldehyde/p-hydroxybenzaldehyde: 0.1 gm; nitro methane: 8 mL; Catalyst: 0.01 gm; Temp:—90° C. T-toluene, IPA-Isopropyl alcohol

Example 11

Oxidation of Olefines Reaction

The liquid phase oxidation of olefines was carried out in a two necked round bottom flask fitted with water condenser charged with olefines (2.5 mmol) and oxidant (5 mmol)- and 10 wt % of catalyst to substrates acid functionalized carbon microspheres as prepared in example-14. The reaction was initiated by immersing in a thermostat oil bath at 80° C. and stirring at 600 pm. The reaction was carried out for 48 h. The samples were withdrawn periodically and analysed on Agilent 6890 Gas chromatograph. It gave 90% conversion and 96% selectivity to epoxide as major product.

| Sr. No. | Substrate | Oxidant | Structure of product | Time (hr) | Conversion (%) | Selectivity (%) Epoxide |
|---|---|---|---|---|---|---|
| 1 | hexene ring | H$_2$O$_2$ | epoxide | 48 | 90 | 96 |
| 2 | octene ring | H$_2$O$_2$ | epoxide | 28 | 94 | 100 |
| 3 | cyclohexadiene | H$_2$O$_2$ | epoxide | 48 | 78 | 80 |
| 4 | cyclooctadiene | H$_2$O$_2$ | epoxide | 40 | 96 | 58.4 (mono) |
| 5 | cyclopentene | H$_2$O$_2$ | epoxide | 60 | 45 | 75 |

Advantages of Invention:

The major advantages of this process are as follows:
1. Simple, inexpensive synthetic procedure for functionalization of active groups onto surface of carbon and better catalyst
2. Use of simple source of bio-derived sugars
3. Grafting of various catalytically active functional groups onto the carbon microsphere such as NH$_2$, COOH.
4. Formation of C—N bond reaction
5. Formation of C—O bond reaction
6. Very high selectivity towards epoxide
7. Use of green oxidant and hence environmentally benign process
8. Easily recyclable catalyst.

The invention claimed is:

1. A process for preparation of functionalized carbon microspheres by grafting catalytically active functional groups on to carbon microspheres obtained from bagasse to generate an acidic or basic surface wherein said process comprises the steps of:
   a) heating bagasse, water and oxalic acid at a temperature ranging between 150 to 180° C. for a time period ranging between 6 to 12 hours to obtain carbon microspheres; and
   b) refluxing of carbon microspheres as obtained in step (a) and an organic solvent selected from the group consisting of n-pentane, n-hexane, toluene, and lower alcohols in the presence of a functional group grafting agent at a temperature ranging between 80-120° C. for a time period in the range of 8 to 12 hours to obtain functionalized carbon microspheres, wherein a C—O formation reaction is an epoxidation process which comprises mixing an olefin, an oxidant $H_2O_2$, an organic solvent acetonitrile and amine functionalized carbon microspheres to obtain a reaction mixture followed by immersing the reaction mixture in a thermostat oil bath at a temperature ranging between 60-80° C. for a time period ranging between 24 to 48 hours to obtain an epoxide with yield in the range of 45-90%.

2. The process as claimed in claim 1, wherein the olefin is selected from the group consisting of cyclic olefines selected from the group consisting of Cyclohexene, Cyclococetene, 1,3 cyclohexene, Pentene, and 1,5 cyclooctadiene.

3. The process as claimed in claim 1, wherein the epoxide is produced from cyclic epoxides selected from the group consisting of Cyclohexeneepoxide, Cycloocene epoxide, Penteneoxide-oxabicyclo[4.1.0]hept-2-ene 1, and Z)-9-oxabicyclo[6.1.0]non-4-ene.

4. The process as claimed in claim 1, wherein a C—N bond formation reaction is a nitroaldol reaction which comprises mixing substituted benzaldehyde selected from the group consisting of benzaldehyde, and p-hydroxybenzaldehyde, nitromethane and amine functionalized carbon microspheres to obtain a reaction mixture followed by immersing the reaction mixture in a thermostat oil bath at a temperature in the range of 70-100° C. for a time period in the range of 0.5 to 35 hours to obtain nitroalcohol and nitrostyrene with yield in the range of 30 to 95% and conversion in the range of 10 to 98%.

\* \* \* \* \*